United States Patent [19]

Kikuchi et al.

[11] Patent Number: 4,912,233

[45] Date of Patent: Mar. 27, 1990

[54] PARA- OR META-TERPHENYLTETRACARBOXYLIC ACID, DIANHYDRIDE THEREOF AND PROCESS FOR PREPARING THE SAME

[75] Inventors: Tohru Kikuchi; Toshiyuki Fujita; Takayuki Saito, all of Hitachi, Japan

[73] Assignee: Hitachi Chemical Company, Ltd., Tokyo, Japan

[21] Appl. No.: 262,220

[22] Filed: Oct. 21, 1988

Related U.S. Application Data

[63] Continuation of Ser. No. 43,187, Apr. 27, 1987, abandoned.

[30] Foreign Application Priority Data

Apr. 30, 1986 [JP] Japan ................... 61-100378
Apr. 30, 1986 [JP] Japan ................... 61-100379

[51] Int. Cl.$^4$ ................... C07C 63/331; C07C 307/89
[52] U.S. Cl. ................... 549/241; 562/410; 562/412; 562/413; 562/415; 562/488
[58] Field of Search ................ 549/241; 562/410, 412, 562/413, 415, 488

[56] References Cited

U.S. PATENT DOCUMENTS

| | | | |
|---|---|---|---|
| 3,270,067 | 8/1966 | Wendler et al. | 562/488 X |
| 3,576,013 | 4/1971 | Cummings | 549/241 |
| 3,891,633 | 6/1975 | Berlin et al. | 549/241 X |
| 4,600,798 | 7/1986 | Cella | 549/241 X |

OTHER PUBLICATIONS

Numata et al., Chemical Abstracts, vol. 106 (1987) 33650x.

*Primary Examiner*—Richard L. Raymond
*Attorney, Agent, or Firm*—Frishauf, Holtz, Goodman & Woodward

[57] ABSTRACT

Disclosed are a para- or meta-terphenyl-3,4,3'',4''-tetracarboxylic acid or a dianhydride and a process for preparing the same. The para- or meta-terphenyl-3,4,3'',4''-tetracarboxylic acid or a dianhydride thereof according to the present invention is a novel compound which is useful as a raw material for a polyimide having higher heat resistance and so on.

7 Claims, 12 Drawing Sheets

PARA- OR META-TERPHENYLTETRACARBOXYLIC ACID, DIANHYDRIDE THEREOF AND PROCESS FOR PREPARING THE SAME

This application is a continuation of application Ser. No. 07/043,187, filed Apr. 27, 1987, abandoned.

BACKGROUND OF THE INVENTION

This invention relates to a novel para- or meta-terphenyltetracarboxylic acid, a dianhydride thereof and a process for preparing the same.

As an aromatic tetracarboxylic acid or a dianhydride thereof, pyromellitic acid or a dianhydride thereof, benzophenonetetracarboxylic acid dianhydride, etc. are known predominantly as a raw material for polyimide resins.

On the other hand, as a terphenyltetracarboxylic acid and para-terphenyl-2,3,2'',3''-tetracarboxylic acid 2,3:2'',3''-dianhydride of the formula (I):

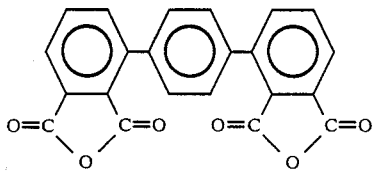

[I]

is known as described in Offenlegungsschrift (West Germany) No. 21 00 391, the Specification of British Patent No. 1,338,932 and the Specification of U.S. Pat. No. 3,891,633.

The tetracarboxylic acid dianhydride of the formula (I) is a compound which can be synthesized through the route illustrated by the following reaction equation (II):

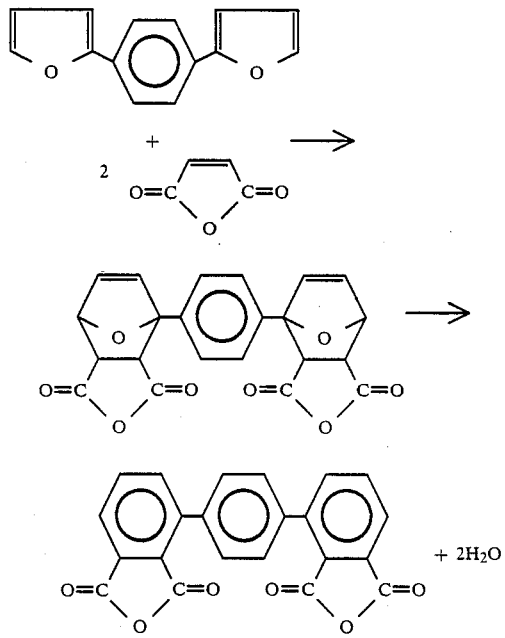

[II]

Namely, in the above reaction, an intermediate compound is obtained through a Diels-Alder reaction between one molecule of 1,4-bis(α-furano)benzene and two molecules of maleic anhydride, and then dehydrated with a concentrated sulfuric acid or a polyphosphoric acid to yield the tetracarboxylic acid dianhydride. Because of the nature of the reaction, the acid anhydride groups come to locate at 2,3- and 2'',3''-positions.

The compound of the formula (I) is used as a cross-linking agent for epoxy resins or phenol-formaldehyde resins.

As meta-terphenyltetracarboxylic acid, there has been reported only one such acid in the Specification of French Patent No. 1,556,159 (Chemical Abastract, Vol. 71, 4960 k), and synthesis thereof can be illustrated by the following reaction equation (III):

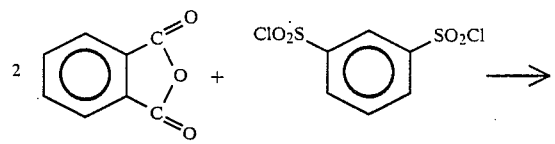

tetracarboxylic acid dianhydride + $SO_2$ + HCl (III)

Namely, in the above reaction, meta-benzenedisulfonyl chloride is reacted with an excess phthalic anhydride under reflux of the latter with generation of sulfur dioxide gas ($SO_2$) and hydrogen chloride gas using copper as a catalyst to yield meta-terphenyltetracarboxylic acid dianhydride. The resulting compound had a melting point m.p. of 130° to 165° C.

While polyimide resins to be obtained from a prior art aromatic tetracarboxylic acid dianhydride and a diamine compound, e.g. diaminodiphenyl ether, diaminodiphenylmethane, etc., are known as a heat-resistant resin, much higher heat resistance is desired with the recent advance of technologies.

Also, the para-terphenyltetracarboxylic acid dianhydride of the abaove formula (I) is known as a crosslinking agent for epoxy resins or phenol resins. However, said para-terphenyltetracarboxylic acid dianhydride has the acid anhydride groups at 2,3- and 2'',3''-positions. Accordingly, the polyimide resin synthesized from said anhydride is difficult to have higher molecular weight, resulting in insufficient heat resistance.

Also, in the above meta-terphenyltetracarboxylic acid dianhydride, the positions of the acid anhydride groups are not definite because of the nature of the synthesis. Besides, in view of the melting point of the resulting compound ranging from as wide as 130° to 165° C., it can be understood that it is a mixture of compounds having acid anhydride groups at different positions. Use of such tetracarboxylic acid dianhydride as a raw material for polyimide resin will result in a polyimide resin of low molecular weight, and its heat resistance is insufficient.

SUMMARY OF THE INVENTION

This invention is directed to provide a novel terphenyltetracarboxylic acid or a dianhydride thereof and a process for preparing the same for the purpose of overcoming the problems in the prior art technologies.

DESCRIPTION OF THE PREFERRED EMBODIMENT

Figure 1:
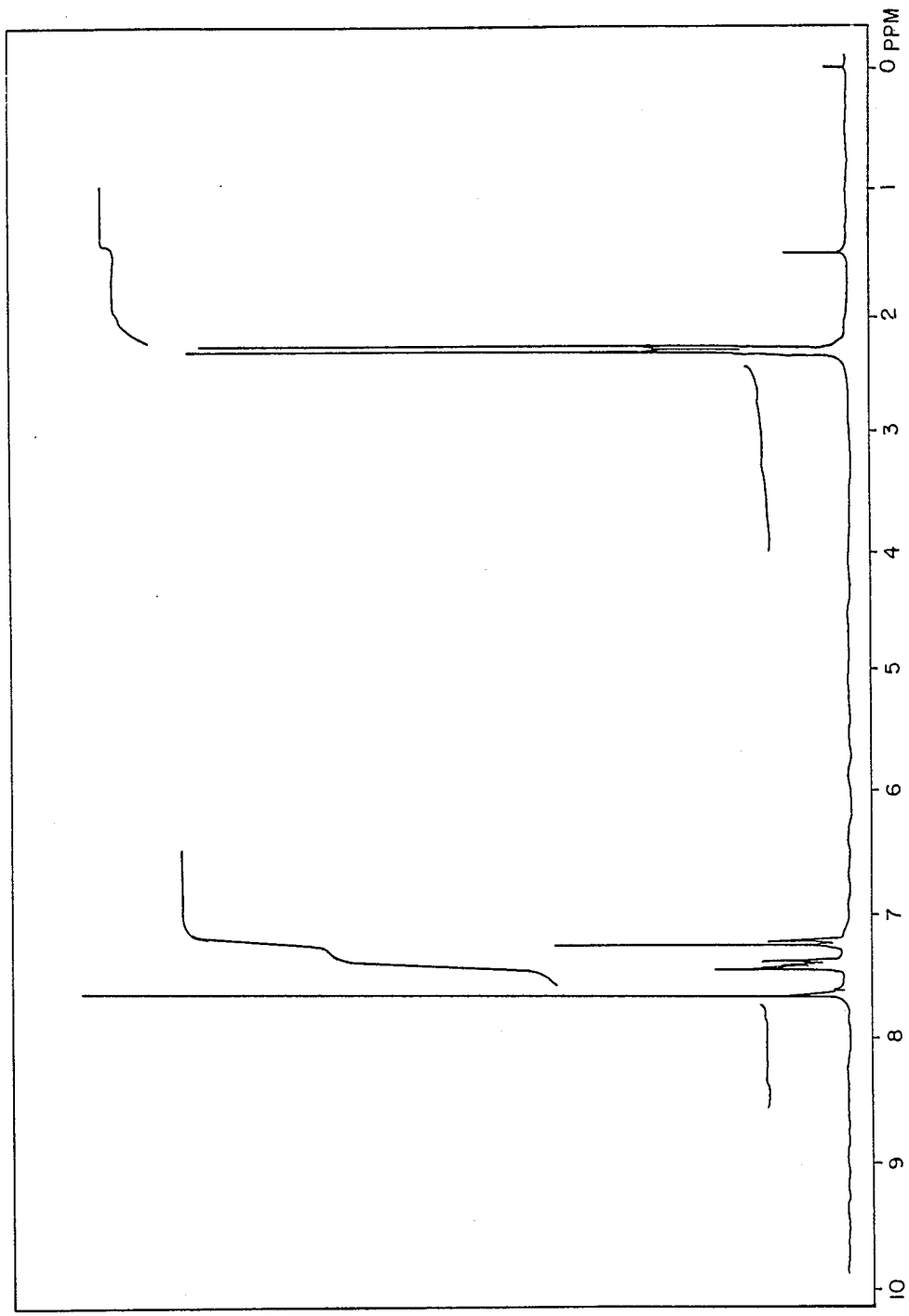
FIG. 1 shows a $^1$H-NMR spectrum of 3,4,3'',4''-tetramethyl-para-terphenyl which is an intermediate in Example 1.

One aspect of this invention relates to para- or meta-terphenyl-3,4,3'',4''-tetracarboxylic acid or a dianhydride thereof.

The para-terphenyl-3,4,3'',4''-tetracarboxylic acid is a compound which can be represented by the following formula (IV):

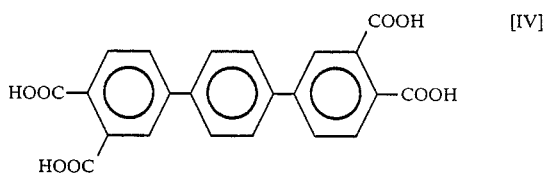

[IV]

Para-terphenyl-3,4,3'',4''-tetracarboxylic acid 3,4:3'',4''-dianhydride, which is a dianhydride of the above compound of the formula (IV), is a compound which can be represented by the following formula (V):

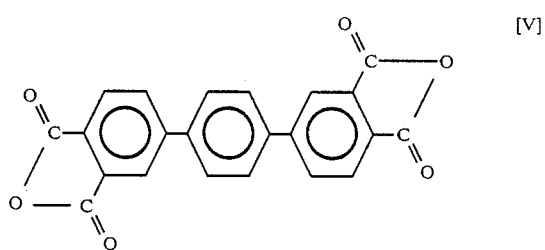

[V]

The para-terphenyltetracarboxylic acid or dianhydride thereof according to this invention has the carboxyl groups or acid anhydride groups located at both ends of the para-terphenyl at 3,4- and 3'',4''-positions thereof, which is a structure different from that of the prior art para-terphenyltetracarboxylic acid dianhydride of the formula (I). Accordingly, it can give a linear structure with the molecules connected in a stretched form, when it is reacted with a diamine compound to yield polyamide acid, and then the polyamide acid obtained is further dehydrated to yield a polyimide resin, thereby giving a polyimide resin having excellent heat resistance.

The meta-terphenyl-3,4,3'',4''-tetracarboxylic acid is a compound which can be represented by the following formula (IV'):

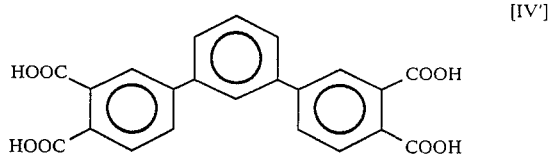

[IV']

Meta-terphenyl-3,4,3'',4''-tetracarboxylic acid 3,4:3'',4''-dianhydride, which is a dianhydride of the abaove compound of the formula (IV'), is a compound which can be represented by the following formula (V'):

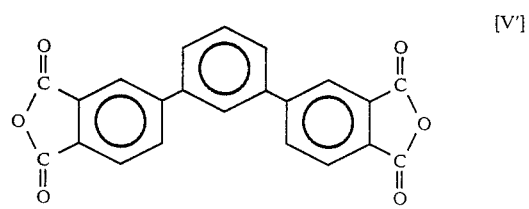

[V']

Because of the fact that the meta-terphenyltetracarboxylic acid or dianhydride thereof according to this invention has the carboxyl groups or acid anhydride groups located at both ends of the meta-terphenyl at 3,4- and 3'',4''-positions thereof, it can give a linear structure with the molecules connected in a stretched linear form, when it is reacted with a diamine compound to yield a polyamide acid, and then the polyamid acid obtained is further dehydrated to yield a polyimide resin, thereby giving a polyimide resin having a high molecular weight and excellent heat resistance.

The meta-terphenyltetracarboxylic acid or the dianhydride thereof according to this invention is a single compound (not a mixture) as can be seen from the Examples given below.

Another aspect of this invention relates to a process for preparing the compound according to this invention.

Namely, the second object of this invention is to provide a process for preparing the para- or meta-terphenyl-3,4,3'',4''-tetracarboxylic acid or dianhydride thereof, comprising oxidizing 3,4,3'',4''-tetramethyl-para- or meta-terphenyl, and if necessary, followed by dehydrative cyclization reaction of the resulting oxidized product.

The above 3,4,3'',4''-tetramethyl-para- or meta-terphenyl can be obtained by subjecting a Grignard reagent of a 4-halogeno-ortho-xylene and a para- or meta-dihalogeno-benzene to double cross-coupling reaction.

The preparation process will be described below in detail.

The para-terphenyltetracarboxylic acid and dianhydride thereof can be prepared through the reaction illustrated by the following reaction equation (VI):

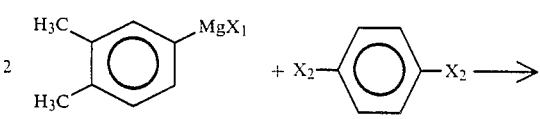

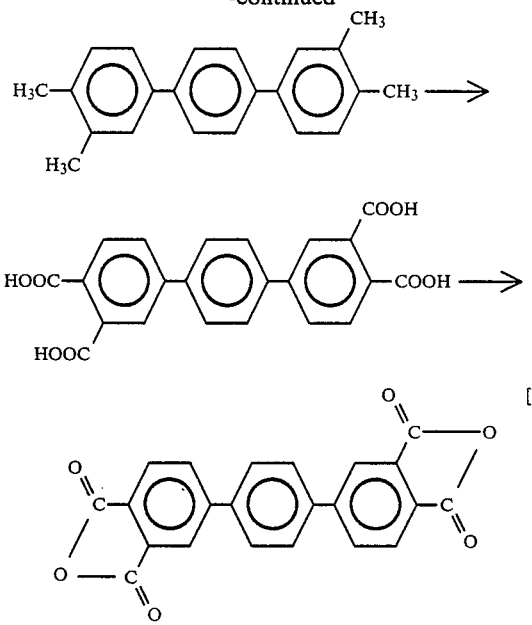

wherein $X_1$ and $X_2$, independent of each other, represent a chlorine, a bromine or a iodine atom.

The meta-terphenyltetracarboxylic acid and dianhydride thereof can be prepared from the reaction illustrated by the following reaction equation (VI'):

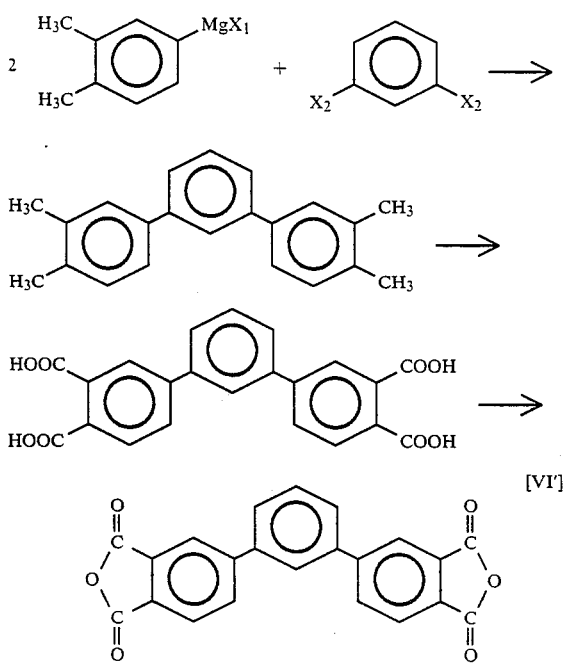

wherein $X_1$ and $X_2$, independent of each other, represent a chlorine, a bromine or an iodine atom.

Namely, in the above reactions, the 4-halogeno-ortho-xylene is reacted with a metallic magnesium according to a customary method to produce a Grignard reagent, and then a para- or meta-dihalogenobenzene and a nickel metal complex catalyst are added to the Grignard reagent thus obtained to yield teteramethyl-para-terphenyl through double cross-coupling reaction. The resulting intermediate, 3,4,3″,4″-tetramethyl-para- or meta-terphenyl is oxidized with a permanganate salt or nitric acid, or by liquid phase air oxidization to yield para- or meta-terphenyl-3,4,3″,4‴-tetracarboxylic acid, which is further heated or treated with acetic anhydride to yield para- or meta-terphenyl-3,4,3″,4″-tetracarboxylic acid 3,4:3″,4″-dianhydride. Alternatively, the above dianhydride can be obtained directly by subjecting 3,4,3″,4″-tetramethyl-para-terphenyl to gas phase oxidization.

The above process will be desdribed below in more detail.

The 4-halogeno-ortho-xylene includes 4-iodo-orthoxylene, 4-bromo-ortho-xylene, etc.

In the procedure of obtaining the Grignard reagent from the 4-halogeno-ortho-xylene, 1.0 gram atom or more of metallic magnesium is used relative to 1.0 mole of the 4-halogeno-ortho-xylene to form the Grignard reagent. In cases where the amount of the metallic magnesium is less than 1.0 gram atom, the unreacted 4-halogeno-ortho-xylene will remain to react with the Grignard reagent of the 4-halogeno-ortho-xylene to form undesired tetramethylbiphenyl unfavorably. The reaction for obtaining the Grignard reagent is conducted typically at a temperature of 0° C. or more and below the reflux temperature of a solvent used, and the reaction time is typically 1 to 10 hours.

If the amount of the metallic magnesium used for the reaction exceeds 1.0 gram atom relative to 1.0 mole of the 4-halogeno-ortho-xylene, the unreacted metallic magnesium will remain, which is then removed by filtration. The solvent to be used in the above reaction includes methyl ether, tetrahydrofuran, etc.

The para-dihalogenobenzene includes para-dibromobenzene, para-dichlorobenzene, etc. By use of para-dichlorobenzene, inter alia, a higher yield will be obtained from the double cross-coupling reaction.

The meta-dihalogenobenzene includes meta-dibromobenzene, meta-dichlorobenzen e, etc. By use of meta-dichlorobenzene, inter alia, a higher yield will be obtained from the double cross-coupling reaction.

The para- or meta-dihalogenobenzene is used in an amount of 0.5 mole relative to 1.0 mole in terms of the 4-halogeno-ortho-xylene component in the Grignard reagent. If said amount is less than 0.5 mol, a residual unreacted Grignard reagent will be present after completion of the reaction, which will be hydrolyzed to form ortho-xylene upon subsequent water washing to reduce the yield of the desired product, although it does not interfere the reaction. On the other hand, if said amount exceeds 0.5 mole, undesired poly-para-phenylene will be formed as a by-product in larger amount.

The nickel metal complex catalyst includes dichlorobis(triphenylphosphine)nickel, dibromobis(triphenylphosphine)nickel, diiodobis(triphenylphosphine)nickel, dichloro[1,2-bis(diphenylphosphino)ethane]nickel, dibromo[1,2-bis(diphenylphosphino)ethane]nickel, dichloro[1,3-bis(diphenylphosphino)propane]nickel, dibromo[1,3-bis(diphenylphosphino)propane]nickel, etc.

The nickel metal complex catalyst may preferably be used in an amount of 0.1 to 1.0% by weight relative to the Grignard reagent in terms of the amount of the 4-halogeno-ortho-xylene component in the Grignard reagent.

The double cross-coupling reaction may preferably be conducted at 20° to 60° C., and the reaction time is usually 1 to 5 hours. Use of low reaction temperature simply leads to longer reaction time, causing no substantial problem. However, if the reaction temperature exceeds 60° C., components having a high boiling point such as polyphenylene, and by-products such as tetramethylbiphenyl are liable to be formed in larger amounts.

After completion of the reaction, the magnesium salt is removed by washing with water. The resulting intermediate, 3,4,3'',4'''-tetramethyl-para-terphenyl, may be purified, if necessary, by recrystallization procedure using toluene, xylene, etc. as a solvent. The intermediate 3,4,3'',4'''-tetramethyl-meta-terphenyl can be purified, if necessary, by washing with ethanol etc.

The intermediate, 3,4,3'',4'''-tetramethyl-para- or meta-terphenyl, may be oxidized to give para- or meta-terphenyl-3,4,3'',4'''-tetracarboxylic acid according to this invention.

Next, an oxidization procedure using permanganate salt will be described below.

As the permanganate salt, potassium permanganate etc. is use. The solvent employed herein is a mixed solution of water and pyridine, preferably in a weight ratio of water to pyridine of 1.0:0.5 to 2.0. To 100 g of this solution, 5 to 15 g of 3,4,3'',4'''-tetramethyl-para- or meta-terphenyl is added, and to the resulting mixture is added slowly 12-fold moles of potassium permanganate. The oxidization reaction may not be completed by use of less than 12-fold moles of the permanganate. The reaction is conducted at a temperature of 50° C. or more and not higher than the reflux temperature (93° C.), usually for 5 to 10 hours. In this reaction, the potassium permanganate is converted to a solvent-insoluble manganese oxide, which is then removed by filtration. The filtrate is subjected to acid precipitation treatment with a concentrated hydrochloric acid since it contains para- or meta-terphenyl-3,4,3'',4'''-tetracarboxylic acid having dissolved therein in the form of a potassium salt. However, since the filtrate also contains pyridine, the pyridine is distilled off in a rotary evaporator prior to the acid precipitation. The concentrated hydrochloric acid is added in an amount such that the pH of the solution may be 1, to give a white crystal of para- or meta-terphenyl-terphenyl-3,4,3'',4'''-tetracarboxylic acid. In the above treatment, since said crystal is allowed to separate out from an aqueous solution, the resulting para- or meta-terphenyl-3,4,3'',4'''-tetracarboxylic acid compound comes to be hydrated with two molecules of water (crystal water).

The thus obtained para- or meta-terphenyl-3,4,3'',4'''-tetracarboxylic acid can be converted to para- or meta-terphenyl-3,4,3'',4'''-tetracarboxylic acid 3,4:3'',4'''-dianhydride according to a method in which said para- or meta-terphenyl-3,4,3'',4'''-tetracarboxylic acid is heated at 120° C. to 250° C. under a reduced pressure of 5 to 50 mmHg for 1 to 24 hours; to a method in which 30 to 60 g of acetic anhydride is added relative to 1 g of said para- or meta-terphenyl-3,4,3'',4'''-tetracarboxylic acid, and then the resulting mixture is refluxed for 0.5 to 2 hours with heating, followed by filtration using a hot funnel and subsequent recrystallization; or to other methods.

The para- or meta-terphenyl-3,4,3'',4'''-tetracarboxylic acid or dianhydride thereof according to this invention is useful as a raw material for polyimide resins and resins of other kinds, or as a curing agnnt for epoxy resins, phenol resins, etc.

The present invention will be explained in more detail by way of the Examples shown below, which, however, should not be construed to limit the present invention.

[EXAMPLE]

In the following, "%" means "% by weight".

EXAMPLE 1

(1) Preparation of Grignard reagent

A two liter four-necked flask equipped with an Allihn condenser, a dropping funnel, a thermometer and a stirrer was dried sufficiently under an argon gas atmosphere and then charged with 100 ml of tetrahydrofuran dried with metallic sodium, 9.72 g of metallic magnesium and 10.0 g of bromo-ortho-xylene (a mixture of 75% of 4-bromo-ortho-xylene and 25% of 3-bromo-orthoxylene). When the reaction mixture became turbid and a Grignard reagent started to be produced, a mixture of 64.0 g of bromo-ortho-xylene of which composition was the same as above and 100 ml of tetrahydrofuran was added dropwise through the dropping funnel over 1 hour. During this procedure, since an exothermic reaction was caused, the reaction temperature was maintained at 40° C. under cooling with an ice bath. Since metallic magnesium remained even after completion of the dropwise addition, the mixture obtained was heated with an oil bath and stirred for 5 hours while maintaining the temperature at 40° C., whereby the metallic magnesium was allowed to react completely to prepare a Grignard reagent.

(2) Preparation of 3,4,3'',4'''-tetramethyl-para-terphenyl

Into a flask, 0.37 g of dichloro[1,2-bis(diphenylphosphino)ethane]nickel catalyst (0.5% based on the total amount of the above bromo-ortho-xylene) was charged and a solution of 29.4 g (0.200 mol) of para-dichlorobenzene dissolved in 85 ml of tetrahydrofuran was added dropwise through a dropping funnel over 1 hour. During this procedure, the reaction temperature was maintained at 35° C. After completion of the dropwise addition, while maintaining the temperature at 35° C., stirring was continued for further 1 hour to complete the double-cross coupling reaction.

After completion of the reaction, 300 ml of toluene was added to the reaction mixture and then 150 ml of deionized water was gradually added over 1 hour under stirring. After the underlying aqueous layer was removed with a separatory funnel, the overlying toluene layer was heated and filtered using a hot funnel. The filtrate wa allowed to stand for cooling to precipitate colorless foil-like crystal. The crystal was collected by filtration and dried to give 26.8 g of crystals.

Figure 2:
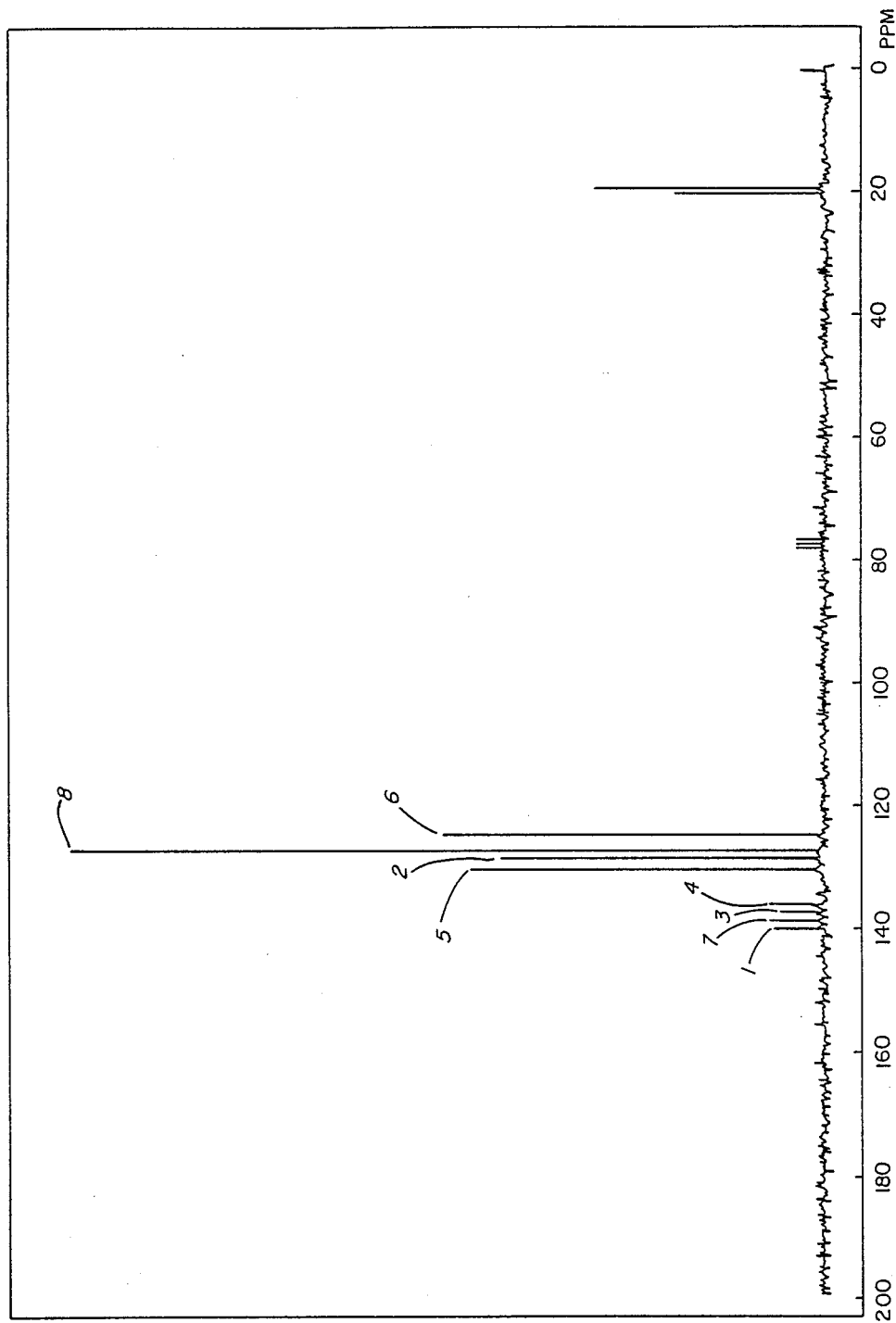
FIG. 2 a $^{13}$C-NMR spectrum of 3,4,3'',4''-tetramethyl-para-terphenyl.

The melting point of the crystal was 168° to 169° C. The proton nuclear magnetic resonance ($^1$H-NMR) spectrum and the carbon nuclear magnetic resonance ($^{13}$C-NMR) spectrum of the product are shown in FIG. 1. In FIG. 1, the integrated intensity ratio of absorption based on 2.29 ppm and 2.32 ppm of methyl group protons to absorption based on 7.17 to 7.65 ppm of benzene ring protons is 180:150 (=12:10), which corresponds approximately to the theoretical value. In FIG. 2, from the fact that only the 10 peaks appear, it can be understood that the compound obtained (theoretical carbon number: 22) has a symmetric structure. Further, the absorptions 1 to 8 appear in FIG. 2, which is consistent enough with expected values of chemical shift of a benzene ring carbon calculated by the Savitzky rule with respect to the benzene ring carbons Nos. 1 to 8 of the compound represented by the formula [VII]:

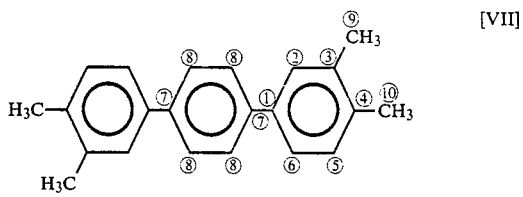

From the foregoing, it could be confirmed that the above crystal was 3,4,3″,4″-tetramethyl-para-terphenyl.

(3) Preparation of para-terphenyl-3,4,3″,4″-tetracarboxylic acid

Into a one liter four-necked flask equipped with an Allihn condenser, a thermometer and a stirrer, 14.3 g (50 mmol) of 3,4,3″,4″-tetramethyl-para-terphenyl, 200 g of pyridine and 200 g of deionized water were charged and the mixture in the flask was heated to 80° C. To the mixture, 110.7 g (700 mmol) of potassium permanganate was gradually added over 3 hours and then stirring was continued for further 5 hours while maintaining the temperature at 80° C. After the precipitate of manganese oxide produced in the reaction was removed by filtration and the pyridine in the filtrate was evaporated with a rotary evaporator, the mixture obtained was subjected to acid precipitation with 36% hydrochloric acid to separate white fine crystal. At this time, the pH of the solution was 1. After filtration and washing with water were repeated twice, the solution was dried under reduced pressure to give 11.6 g of white powdery crystal.

Figure 3:
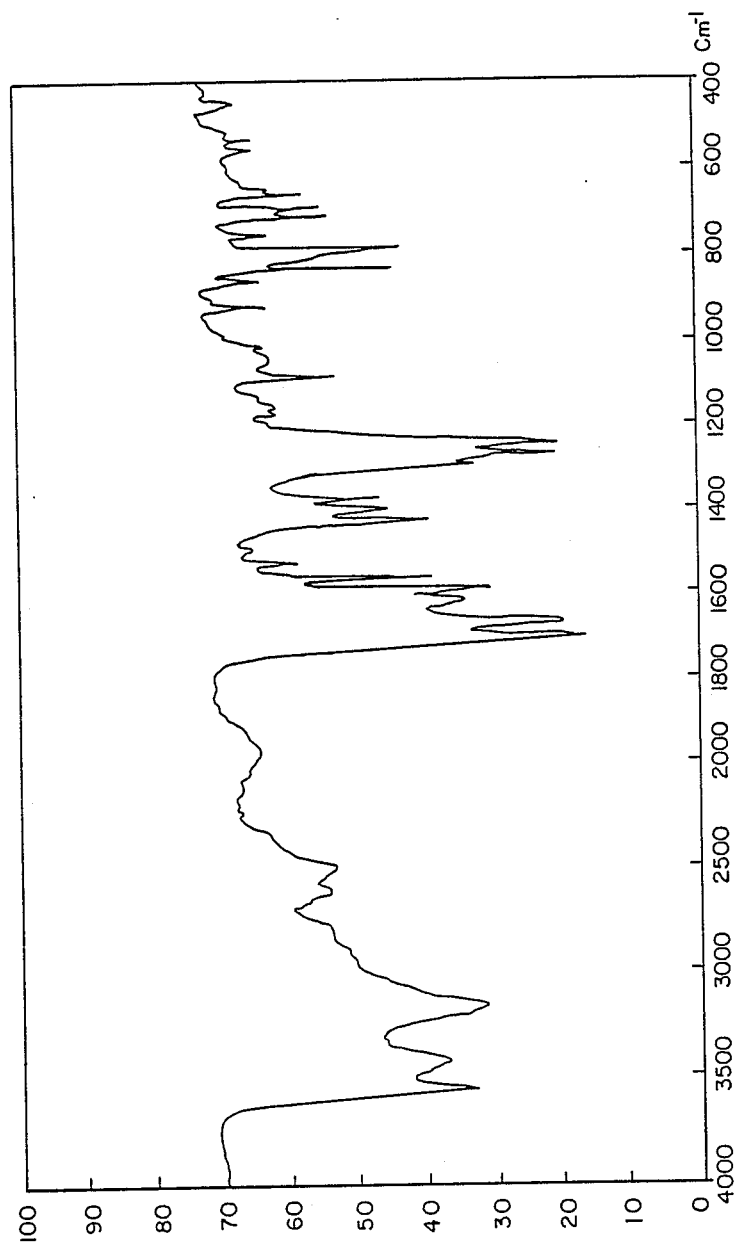
FIG. 3 an infrared absorption spectrum of para-terphenyl-3,4,3'',4''-tetracarboxylic acid.
Figure 4:
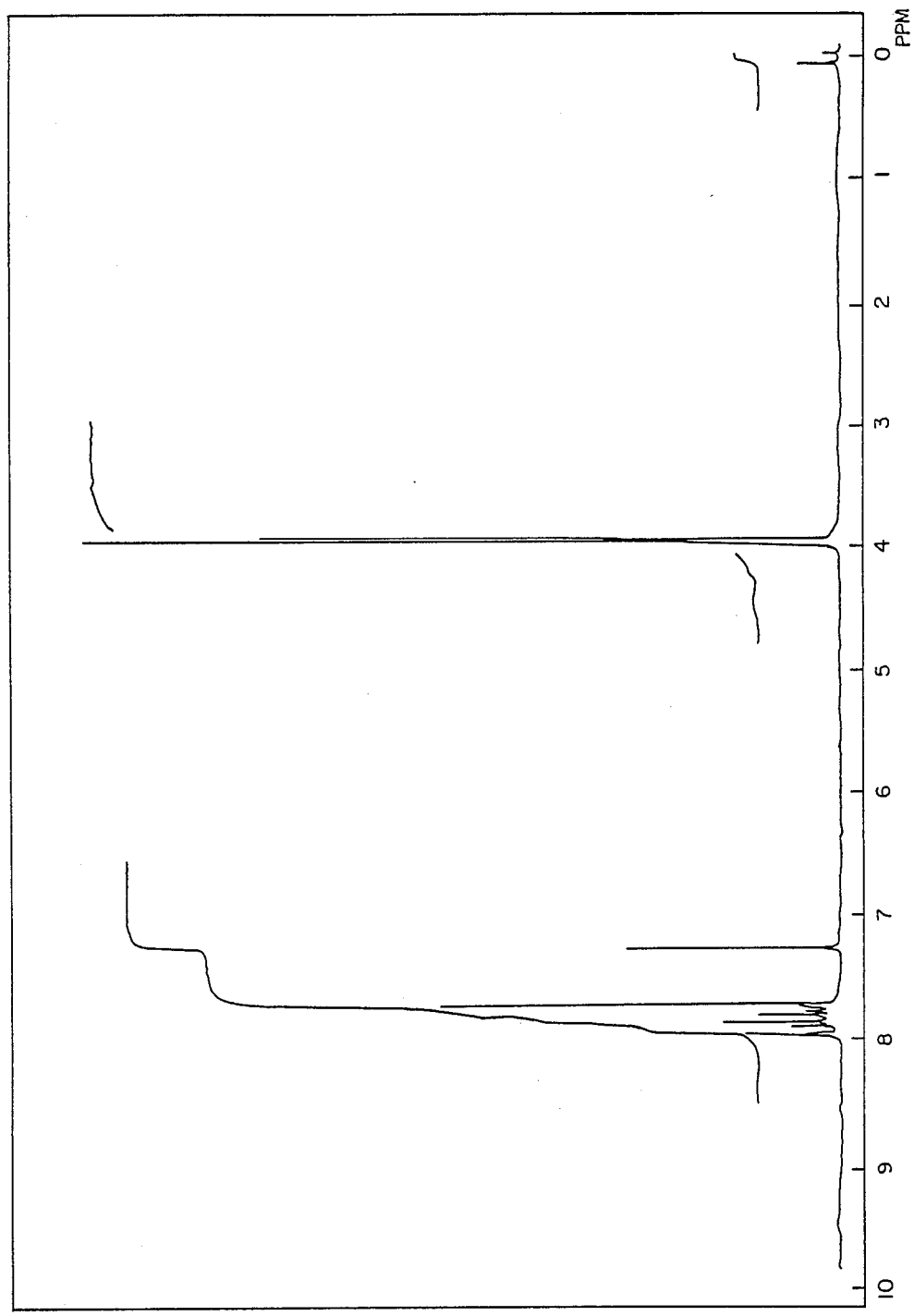
FIG. 4 an $^1$H-NMR spectrum of para-terphenyl-3,4,3'',4''-tetracarboxylic acid tetramethyl ester.

The melting point of the crystal was 311° to 313° C. The infrared absorption spectrum thereof is shown in FIG. 3. To the crystal, were added 50 ml of methanol and 2 ml of 97% sulfuric acid per 0.4 g of the crystal and the resulting mixture was refluxed for 8 hours to conduct methyl esterification of the above crystal. The result of $^1$H-NMR spectrum of the methyl esterified product obtained is shown in FIG. 4. In FIG. 4, the integrated intensity ratio of absorption based on 3.91 ppm and 3.94 ppm of methyl group protons to absorption based on 7.71 to 7.95 ppm benzene ring protons is 180:151 (=12:10.07 ), which corresponds approximately to the theoretical value (the methyl-esterified compound of the compound of Formula [IV]).

Further, the elemental analysis of the above crystal was conducted to obtain the results shown below.

Found value: Carbon: 59.67%, Hydrogen: 4.15%.

Theoretical value: Carbon: 65.03%, Hydrogen: 3.47%. (be noted that the theoretical values are those determined with respect to the compound of Formula [V]).

As a result of the elemental analysis, since the found values were different from the theoretical value, a thermogravimetry-differential thermal analysis of the above crystal was conducted at a rate of temperature elevation of 5° C./min. The endothermic peaks were obtained at 160° C., 230° C. and 310° C. At 160° C. and 230° C., weight loss of 17% in total was observed. Although the endothermic peak at 310° C. was caused by the melting, the endothermic peaks at 160° C. and 230° C. were brought about by dehydration. If dehydration and ring closure of para-terphenyl-3,4,3″,4″-tetracarboxylic acid are caused by heat during the differential thermal balance analysis to convert it merely into the corresponding acid anhydride, reduction in weight should be 9%. Accordingly, the crystal obtained is considered to have water of crystallization and the found values of the above elemental analysis are extremely consistent with theoretical values of the elemental analysis, i.e. carbon: 59.73%, hydrogen: 4.10%, in the case where two molecules of water of crystallization are hydrated in the compound of Formula [IV].

From the foregoing, it was confirmed that the above crystal was para-terphenyl-3,4,3″,4″-tetracarboxylic acid and had two molecules of crystal water.

Figure 5:
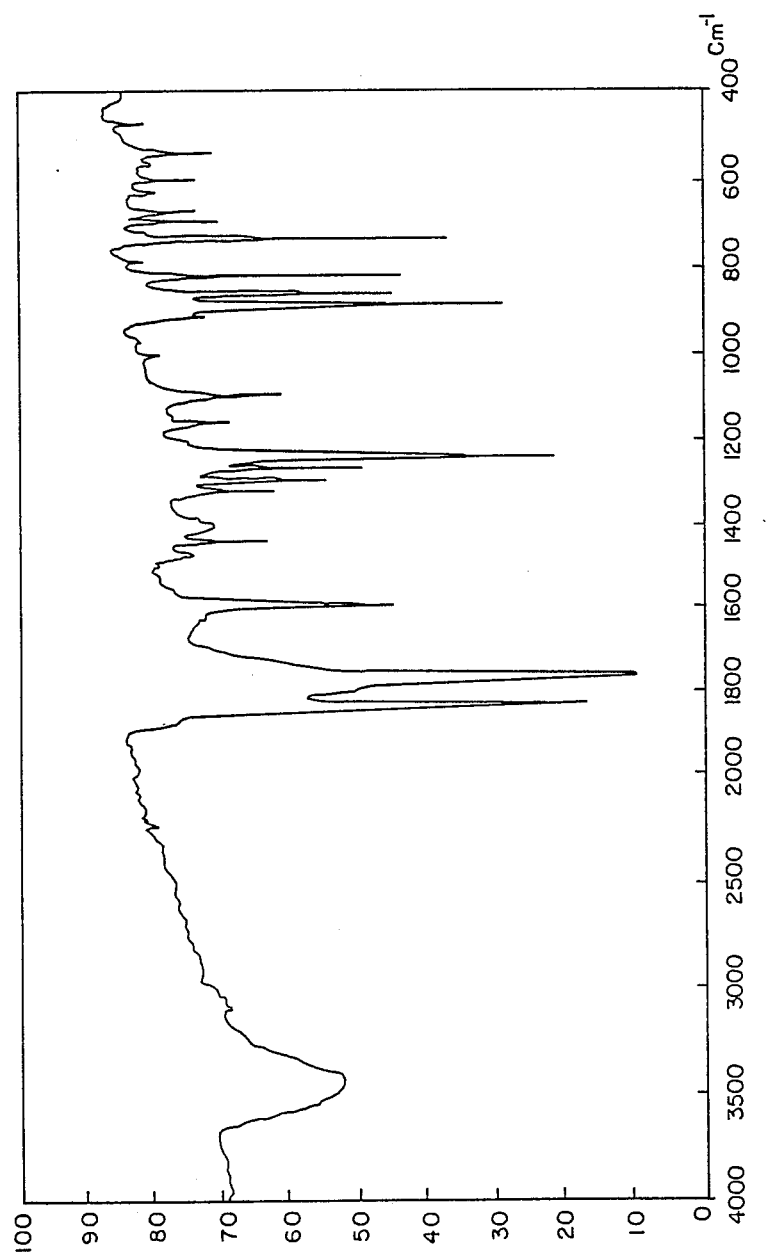
FIG. 5 an infrared absorption spectrum of para-terphenyl-3,4,3'',4''-tetracarboxylic acid 3,4:3'',4''-dianhydride.
Figure 6:
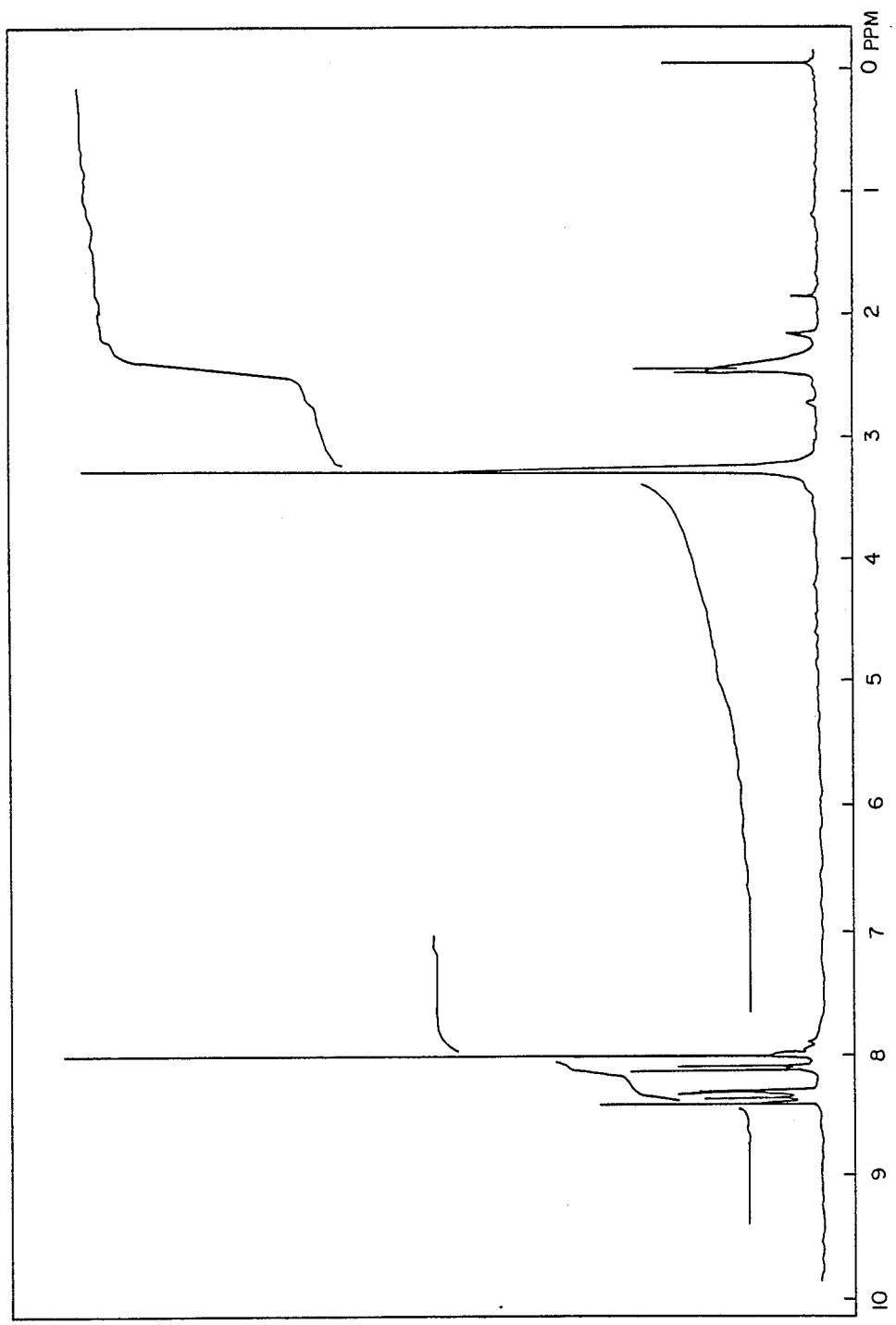
FIG. 6 a $^1$H-NMR spectrum of para-terphenyl-3,4,3'',4''-tetracarboxylic acid 3,4:3'',4''-dianhydride.

(4) Preparation of para-terphenyl-3,4,3″,4″-tetracarboxylic acid 3,4,3″,4″-dianhydride Into a one liter pear-shaped flask, 10.0 g of the above crystal and 400 g of acetic anhydride were charged and the mixture was dissolved by heating under reflux for 30 minutes and then filtered using a hot funnel. The filtrate was allowed to stand for cooling to separate light brown powdery fine crystal. The reaction mixture was filtered and dried under reduced pressure to give 6.9 g of powdery crystal. The infrared absorption spectrum and $^1$H-NMR spectrum of the powdery crystal are shown in FIG. 5 and FIG. 6, respectively.

The melting point of the crystal was 311° to 313° C. As a result of the elemental analysis, carbon was 71.28% and hydrogen was 2.76%, which were consistent enough with the theoretical values (the compound of Formula [V]), i.e. carbon: 71.36%, hydrogen: 2.72%. It was confirmed thereby that the crystal was para-terphenyl-3,4,3″,4″-tetracarboxylic acid 3,4:3″,4″-dianhydride.

EXAMPLE 2

(1) Preparation of Grignard reagent as in (1) of Example 1.

(2) Preparation of 3,4,3″,4″-tetramethyl-meta-terphenyl

Into a flask, 0.37 g of dichloro[1,2-bis-(diphenylphosphino)ethane]nickel catalyst (0.5% of bromo-orthoxylene) was charged and a solution of 29.4 g (0.200 mol) of meta-dichlorobenzene dissolved in 85 ml of tetrahydrofuran was added dropwise from a dropping funnel over 1 hour. During this procedure, the reaction temperature was maintained at 35° C. After completion of the dropwise addition, while maintaining the temperature at 35° C., stirring was continued for further 1 hour to complete the double-cross coupling reaction.

After completion of the reaction, 300 ml of toluene was added to the mixture and then 150 ml of deionized water was added gradually over 1 hour under stirring. After the underlying aqueous layer was removed with a separatory funnel, the overlying toluene layer was dried up with a rotary evaporator. After allowed to stand for cooling, the crystal separated was collected and washed three times with ethanol, followed by drying under reduced pressure, to give 24.4 g of colorless plate-like crystal.

Figure 7:
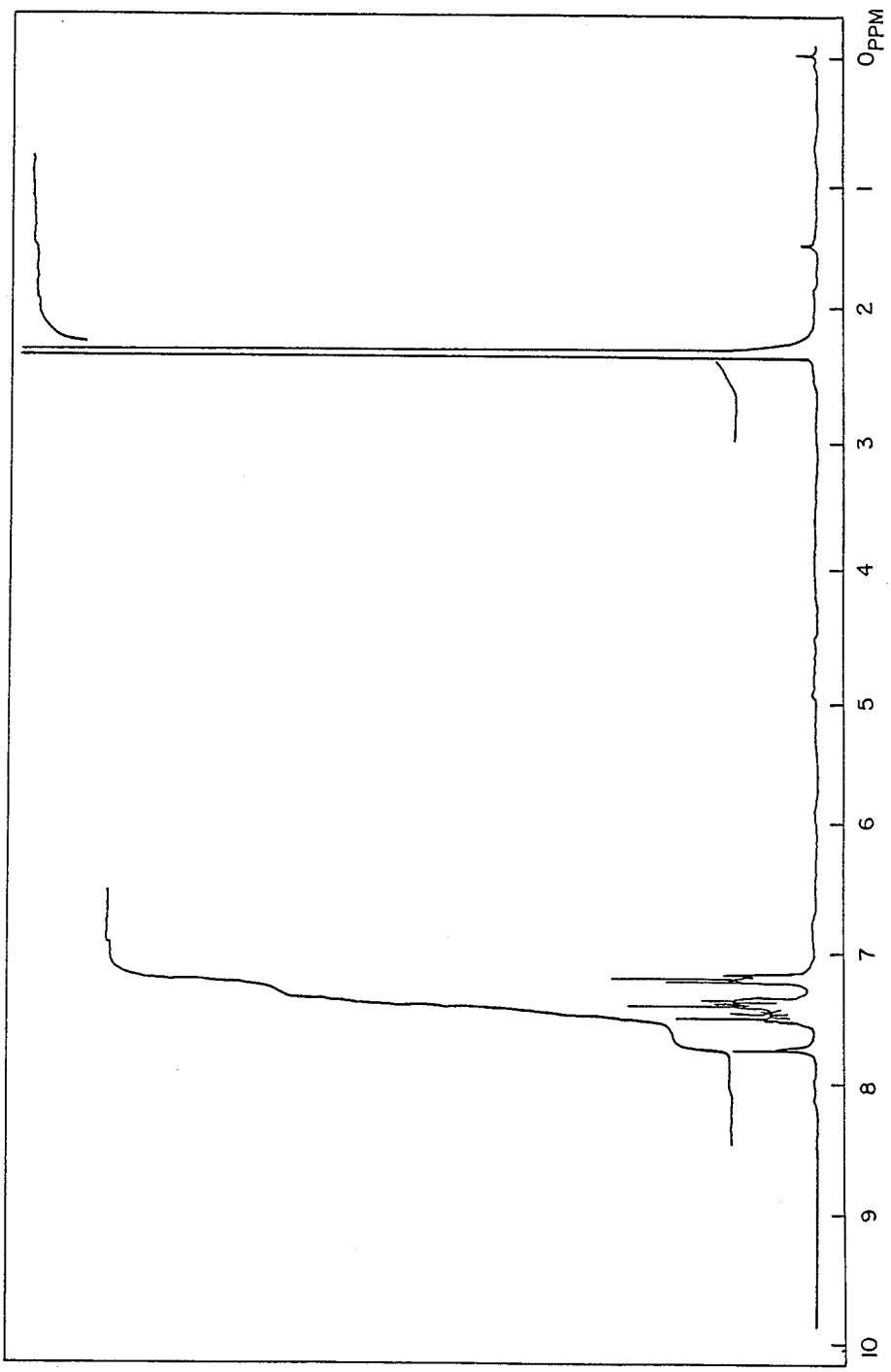
FIG. 7 shows a $^1$H-NMR spectrum of 3,4,3'',4''-tetramethyl-meta-terphenyl which is an intermediate in Example 2.
Figure 8:
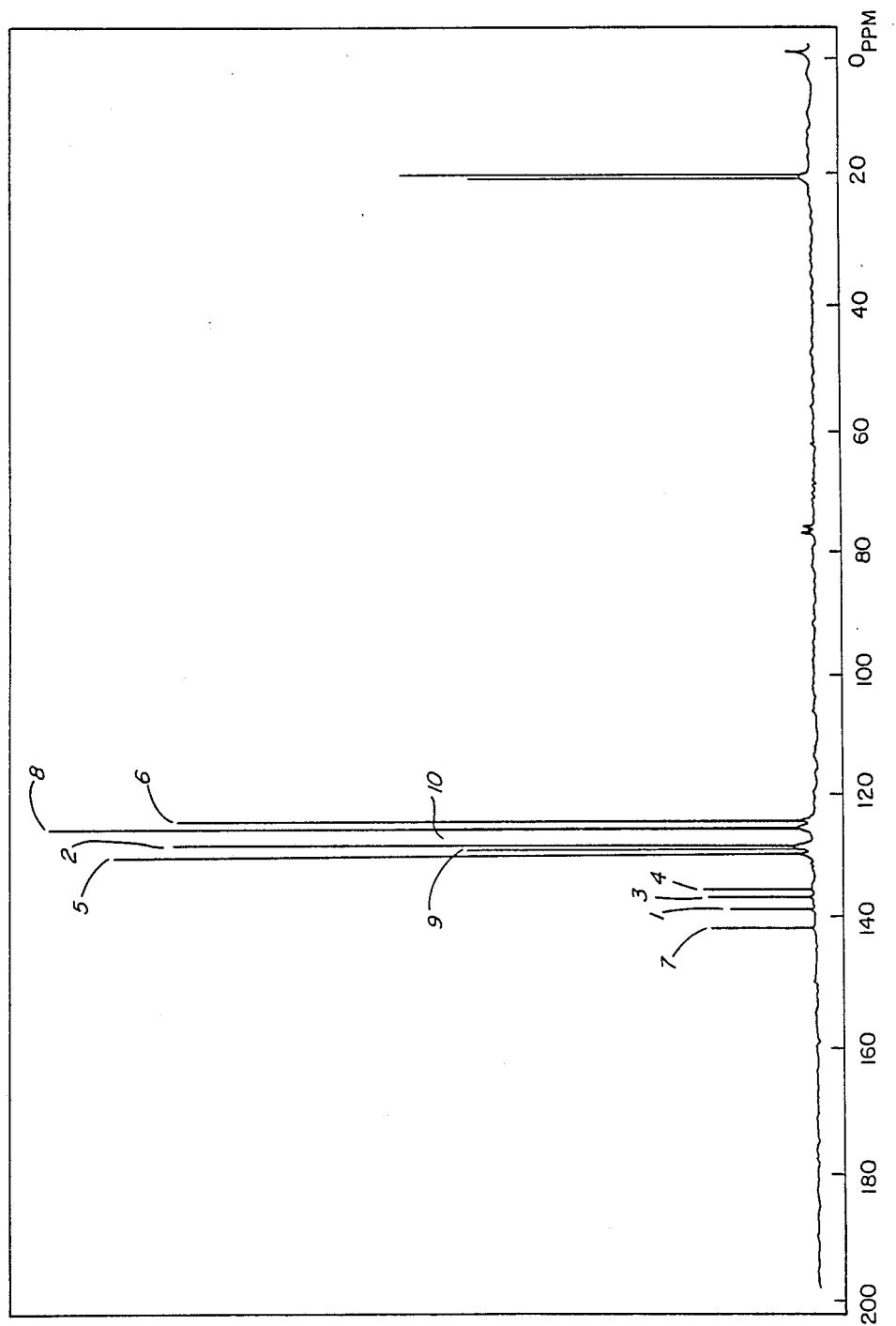
FIG. 8 a $^{13}$C-NMR spectrum of 3,4,3'',4''-tetramethyl-meta-terphenyl.

The melting point of the crystal was 72° to 73° C. The results of the proton nuclear magnetic resonance ($^1$H-NMR) spectrum and the carbon nuclear magnetic resonance ($^{13}$C-NMR) spectrum are shown in FIG. 7 and FIG. 8, respectively. In FIG. 7, the integrated intensity ratio of the absorption based on 2.29 ppm and 2.32 ppm of methyl group protons to the absorption based on 7.17 to 7.76 ppm of benzene ring protons is 180:150 (=12:10), which corresponds approximately to the theoretical value. In FIG. 8, from the fact that only the 12 peaks appear, it can be understood that the compound obtained (theoretical carbon number: 22) has a symmetric structure with respect to the benzene ring in the center of terphenyl. Further, the absorptions 1 to 10 appear in FIG. 8, which corresponds approximately to the expected value of chemical shift of the benzene ring carbon calculated by the Savitzky rule with respect to the benzene ring carbons Nos. 1 to 8 of the compound represented by the formula [VIII]:

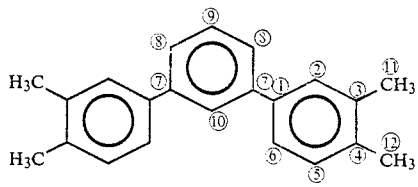

[VIII]

From the foregoing, it was confirmed that the above crystal was 3,4,3'',4''-tetramethyl-meta-terphenyl.

(3) Preparation of meta-terphenyl-3,4,3'',4''-tetracarboxylic acid

Into a one liter four-necked flask equipped with an Allihn condenser, a thermometer and a stirrer, 14.3 g (50 mmol) of 3,4,3'',4''-tetramethyl-meta-terphenyl, 200 g of pyridine and 200 g of deionized water were charged and the mixture within the flask was heated to 80° C. To the mixture, 110.7 g (700 mmol) of potassium permanganate was added gradually over 3 hours and then stirring was continued for further 5 hours while maintaining the temperature at 80° C. After the precipitate of manganese oxide formed in the reaction was removed by filtration and the pyridine in the filtrate was evaporated with a rotary evaporator, the mixture obtained was subjected to acid precipitation with 36% hydrochloric acid to precipitate white fine crystals. The pH of the solution was 1. After filtration and washing with water were repeated twice, the solution was dried under reduced pressure to give 8.9 g of while powdery crystal.

Figure 9:
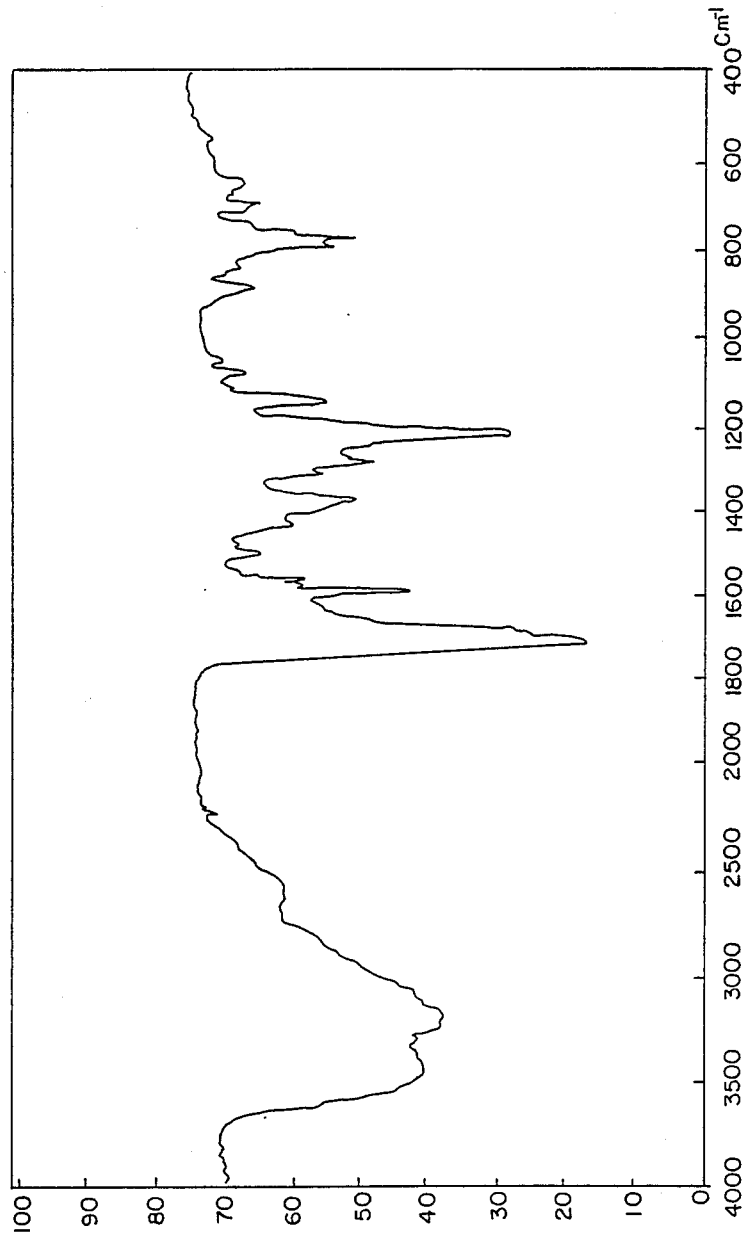
FIG. 9 an infrared absorption spectrum of meta-terphenyl-3,4,3'',4''-tetracarboxylic acid.
Figure 10:
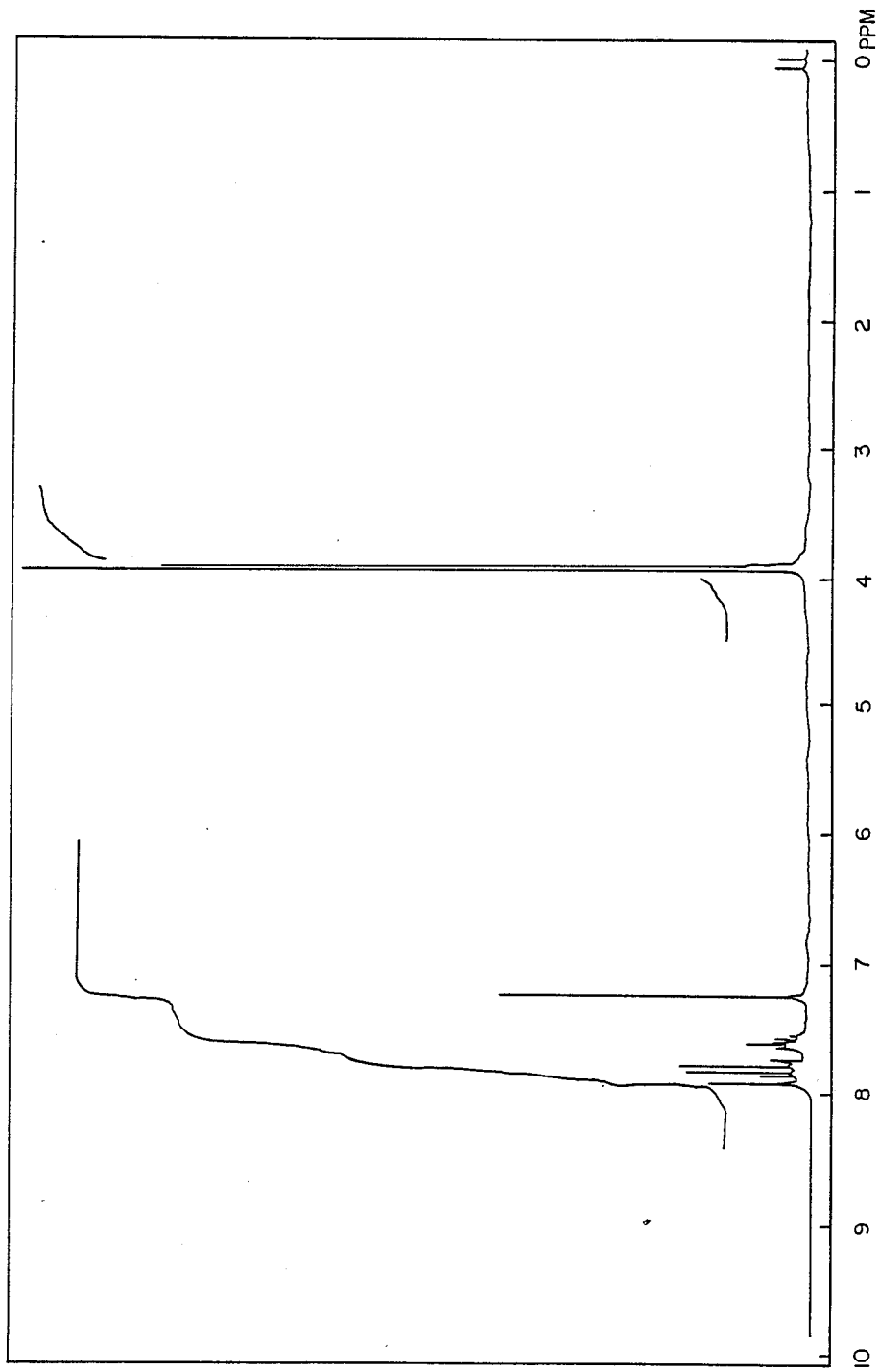
FIG. 10 an $^1$H-NMR spectrum of meta-terphenyl-3,4,3'',4''-tetracarboxylic acid tetramethyl ester.

The melting point of the crystal was 296° to 298° C. The infrared absorption spectrum thereof is shown in FIG. 9. 50 ml of methanol and 2 ml of 97% sulfuric acid per 0.4 g of the crystal were added thereto and the mixture was refluxed for 8 hours to conduct methyl esterification of the above crystal. The result of $^1$H-NMR spectrum of the resulting methyl ester is shown in FIG. 10. In FIG. 10, the integrated intensity ratio of the absorption based on 3.91 ppm and 3.94 ppm of methyl group protons to the absorption based on 7.55 to 7.95 ppm benzene ring protons is 175:147 (=12:10.08), which is consistent enough with the theoretical value (the methyl ester compound of the compound of Formula [IV']).

Further, the elemental analysis of the above crystal was conducted to obtain the results shown below.

Found value: Carbon: 59.65%, Hydrogen: 4.16%.

Theoretical value: Carbon: 65.03%, Hydrogen: 3.47%. (be noted that the theoretical values are those determined with respect to the compound of Formula [V']).

As a result of the elemental analysis, since the found values were different from the theoretical value, a thermogravimetry-differential thermal analysis of the above crystal was conducted at a rate of temperature increase of 5° C./min. The endothermic peaks were obtained at 211° C. and 298° C. At 211° C., weight loss of 17% in total was observed. Although the endothermic peak at 298° C. was brought about by the melting, the endothermic peak at 211° C. was brought about by the dehydration. If dehydration and ring closure of meta-terphenyl-3,4,3'',4''-tetracarboxylic acid are only caused by heat during the differential thermo-gravimetrical analysis to convert it into the corresponding acid anhydride, the weight loss should be 9%. Accordingly, the crystal obtained can be thought to have crystal water and the found values of the above elemental analysis extremely correspond to theoretical values of the elemental analysis, i.e. carbon: 59.73%, hydrogen: 4.10%, in the case where two molecules of crystal water are hydrated in the compound of Formula [IV'].

From the foregoing, it was confimed that the above crystal was meta-terphenyl-3,4,3'',4''-tetracarboxylic acid and had two molecules of crystal water.

Figure 11:
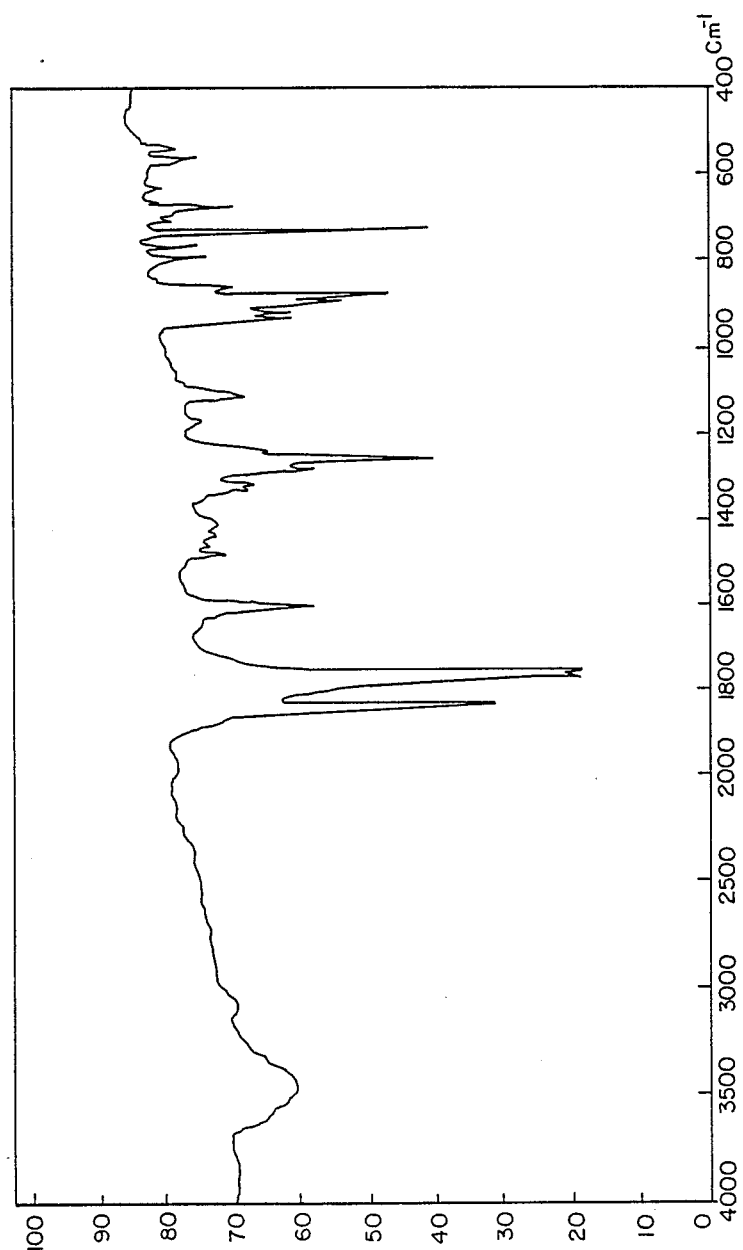
FIG. 11 an infrared absorption spectrum of meta-terphenyl-3,4,3'',4''-tetracarboxylic acid 3,4,3'',4''-dianhydride.
Figure 12:
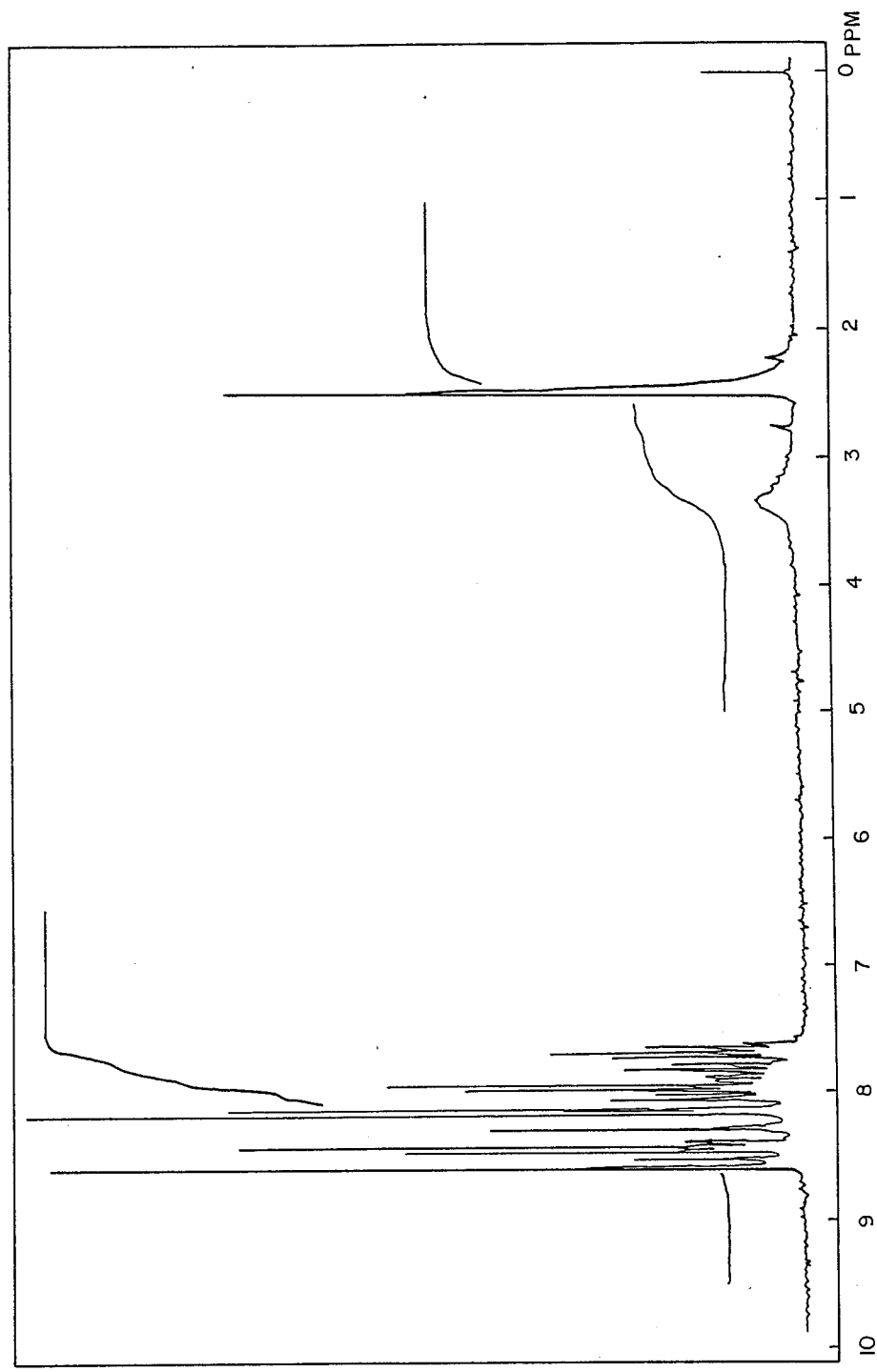
FIG. 12 a $^1$H-NMR spectrum of meta-terphenyl-3,4,3'',4''-tetracarboxylic acid 3,4,3'',4''-dianhydride.

(4) Preparation of meta-terphenyl-3,4,3'',4''-tetracarboxylic acid-3,4,3'',4''-dianhydride Into a one liter pear-shaped flask, 8.00 g of the above crystal was charged and the pressure within the flask was made 20 mmHg with use of a vacuum pump. The flask was immersed in an oil bath of 180° C. for 15 hours to carry out dehydration and ring closure. Thus, 7.29 g of light brown powdery crystal was obtained. An infrared absorption spectrum and $^1$H-NMR spectrum of the powdery crystal are shown in FIG. 11 and FIG. 12, respectively.

The melting point of the crystal was 296° to 298° C. As a result of the elemental analysis, carbon was 71.17% and hydrogen was 2.79%, which corresponds approximately to the theoretical values (the compound of Formula [V]), i.e. carbon: 71.36%, hydrogen: 2.72%. It was confirmed thereby the crystal was meta-terphenyl-3,4,3'',4''-tetracarboxylic acid-3,4:3'',4''-dianhydride.

APPLICATION EXAMPLE 1

Into a 200 ml three-necked flask equipped with a stirrer, 10.0 g (27.0 mmol) of para-terphenyl-3,4,3'',4''-tetracarboxylic acid 3,4,3'',4''-dianhydride obtained in Example 1, 5.41 g (27.0 mmol) of 4,4'-diaminodiphenyl ether and, 87.3 g of N-methylpyrrolidone as a reaction solvent were charged and, under nitrogen atmosphere, the mixture was stirred at 25° C. for 8 hours to prepare a polyamide acid varnish (nonvolatile content: 15% by weight). During the reaction, the maximum viscosity of the polyamide acid varnish was 30 poise (measured at 25° C.).

The polyamide acid varnish obtained was casted on a glass plate and subjected to heat treatment in a thermo-controlled hot-air oven at 150° C. for 1 hour and subsequently at 350° C. for 1 hour to remove the reaction solvent. Also, the polyamide acid was coverted into a polyimide through a dehydration reaction to obtain a polyimide film with a thickness of 40 μm.

The weight loss of the polyimide film after left to stand in air at 460° C. for 30 minutes was 21%. The thermo-gravimetrical analysis (rate of temperature increase: 10° C./min.) revealed that the weight loss started at 472° C.

APPLICATION EXAMPLE 2

Into a 200 ml three-necked flask equipped with a stirrer, 10.0 g (27.0 mmol) of meta-terphenyl-3,4,3'',4''-tetracarboxylic acid-3,4:3'',4''-dianhydride obtained in Example 2, 5.41 g (27.0 mmol) of 4,4'-diaminodiphenyl ether and, 87.3 g of N-methylpyrrolidone as a reaction solvent were charged and, under nitrogen atmosphere, the mixture was stirred at 25° C. for 8 hours to prepare a polyamide acid varnish (nonvolatile content: 15% by weight). During the reaction, the maximum viscosity of the polyamide acid varnish was 3 poise (measured at 25° C.).

The polyamide acid varnish obtained was casted on a glass plate and subjected to heat treatment in a thermo-controlled hot-air oven at 150° C. for 1 hour and at 350° C. for 1 hour to remove the reaction solvent. Also, the polyamide acid was coverted into a polyimide through a dehydration reaction to obtain a polyimide film with a thickness of 40 μm.

The weight loss of the polyimide film after left to stand in air at 460° C. for 30 minutes was 3.2%. The thermo-gravimetrical analysis (rate of temperature elevation: 10° C./min.) revealed that the weight loss started at 464° C.

COMPARATIVE APPLICATION EXAMPLE 8.0 g (36.7 mmol) of pyromellitic acid dianhydride, 7.34 g (36.7 mmol) of 4,4'-diaminodiphenyl ether and 86.9 g of N-methylpyrrolidone were allowed to react in the same manner as in Application example 2 to synthesize a polyamide acid varnish with nonvolatile content of 15% by weight. During the reaction, the maximum viscosity of the polyamide acid varnish was 3,000 poise (measured at 25° C.).

From the polyamide acid varnish obtained, a polyimide film was obtained in the same manner as in Application example 2 and heat resistance of the film was measured. As a result, the weight loss of the film after left to stand in air at 460° C. for 30 minutes was 3.5% by weight and the thermo-gravimetrical analysis (rate of temperature elevation: 10° C./min.) revealed that the reduction in weight started at 460° C.

We claim:

1. A para- or meta-terphenyl-3,4,3'',4'''-tetracarboxylic acid or a dianhydride thereof.

2. The para-terphenyl-3,4,3'',4'''-tetracarboxylic acid of claim 1.

3. The meta-terphenyl-3,4,3'',4'''-tetracarboxylic acid of claim 1.

4. The dianhydride of the para-terphenyl-3,4,3'',4'''-tetracarboxylic acid of claim 1.

5. The dianhydride of the meta-terphenyl-3,4,3'',4'''-tetracarboxylic acid of claim 1.

6. A process for preparing a para- or meta-terphenyl-3,4,3'',4'''-tetracarboxylic acid or a dianhydride thereof, comprising oxidizing 3,4,3'',4'''-tetramethyl-para- or meta-terphenyl, and if necessary, followed by dehydrative cyclization reaction, and wherein the 3, 4, 3'', 4'''-tetramethyl-para-or meta-terphenyl is a product of the double cross-coupling reaction between a Grignard reagent of a 4-halogeno-ortho-xylene and a para-or meta-dihalogeno-benzene in the presence of a nickel catalyst.

7. The process for preparing a para- or meta-terphenyl-3,4,3'',4'''-tetracarboxylic acid or a dianhydride thereof according to claim 6, wherein the para- or meta-dihalogenobenzene is para- or meta-dichlorobenzene.

* * * * *